United States Patent
Layne

(10) Patent No.: US 9,791,094 B1
(45) Date of Patent: Oct. 17, 2017

(54) METHOD AND APPARATUS FOR A PROSTHETIC STAND

(71) Applicant: Thomas Layne, St. Charles, MO (US)

(72) Inventor: Thomas Layne, St. Charles, MO (US)

( * ) Notice: Subject to any disclaimer, the term of this patent is extended or adjusted under 35 U.S.C. 154(b) by 0 days.

(21) Appl. No.: 15/133,130

(22) Filed: Apr. 19, 2016

(51) Int. Cl.
  F16M 11/04 (2006.01)
  F16B 2/22 (2006.01)
  F16M 11/42 (2006.01)

(52) U.S. Cl.
  CPC ............ *F16M 11/046* (2013.01); *F16B 2/22* (2013.01); *F16M 11/42* (2013.01)

(58) Field of Classification Search
  CPC .. A47C 7/00; A47C 7/50; A47C 16/02; F16M 11/046; F16M 11/42; F16B 2/22; A61G 13/12; A61G 13/125; A61G 7/0755; A61G 2005/128; A47B 2200/0098
  USPC ...................................................... 5/624, 651
  See application file for complete search history.

(56) References Cited

U.S. PATENT DOCUMENTS

| | | | | |
|---|---|---|---|---|
| 2,341,080 A | * | 2/1944 | Burkholder | A47C 16/02 211/134 |
| 2,850,342 A | * | 9/1958 | Robinson | A61G 13/12 248/118 |
| 3,556,591 A | * | 1/1971 | Smith | A47C 16/02 297/270.5 |
| 3,704,847 A | * | 12/1972 | Schmitt | A47C 9/025 248/127 |
| 4,641,882 A | * | 2/1987 | Young | A47C 9/025 297/183.1 |
| 4,768,831 A | * | 9/1988 | Liedberg | A47C 9/02 297/344.14 |
| 5,711,334 A | * | 1/1998 | Roux | A61H 3/02 135/65 |
| 5,899,419 A | | 5/1999 | Ross et al. | |
| 6,969,031 B2 | | 11/2005 | Ugent et al. | |
| 9,033,073 B2 | * | 5/2015 | Garcia | B60K 1/04 180/21 |
| 9,474,377 B2 | * | 10/2016 | Keen | A47C 7/506 |
| 2007/0221101 A1 | * | 9/2007 | Schiel | A61F 2/50 108/28 |
| 2010/0007104 A1 | | 1/2010 | Bennett | |
| 2014/0207253 A1 | | 7/2014 | Horton et al. | |

* cited by examiner

Primary Examiner — Christopher E Garft
(74) Attorney, Agent, or Firm — Ari M. Bai; Polsinelli PC

(57) ABSTRACT

Various embodiments of a prosthetics stand having a base with a post that extends upwardly from the base and a holder component coupled to the post and having a pair of holders configured to secure and store one or more lower-extremity prosthetics are disclosed. The pair of holders each defines a circular portion that forms an opening slot configured to allow a lower-extremity prosthetic pass through and be retained within the confines of each respective holder. The prosthetic stand includes a plurality of wheels that allow the prosthetic stand to be mobile and a securing means operable to allow the prosthetics stand to be attached to a structural element, such as a bed or bathtub, to prevent inadvertent movement of the holder component. In some embodiments, the base may have an angled portion that allows the lower-extremity prosthetic to be attached and reattached to an individual in a more natural and convenient manner.

14 Claims, 8 Drawing Sheets

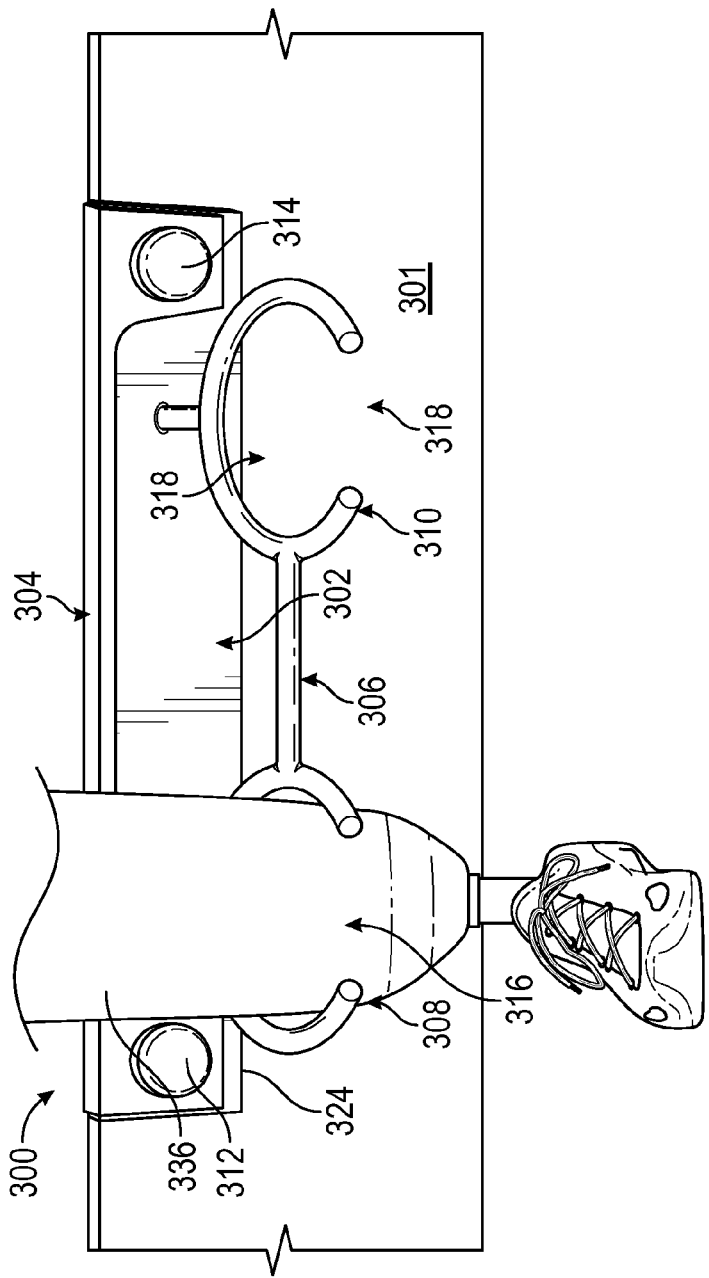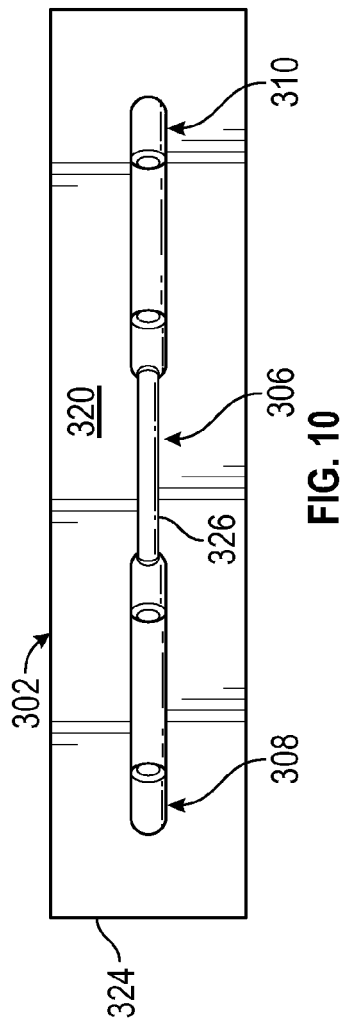

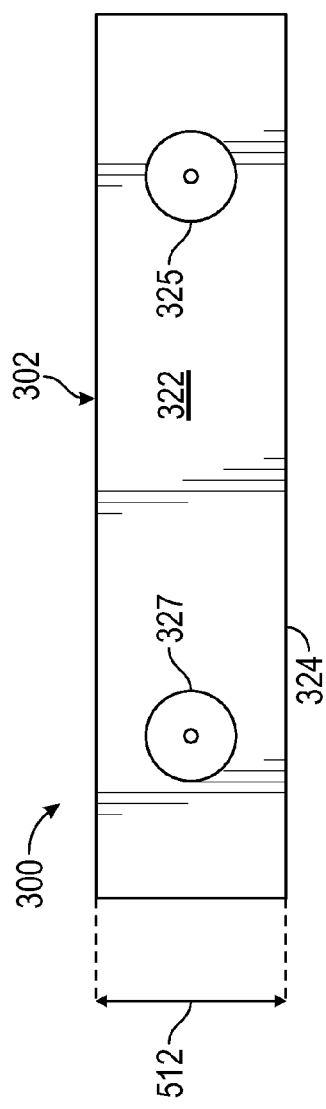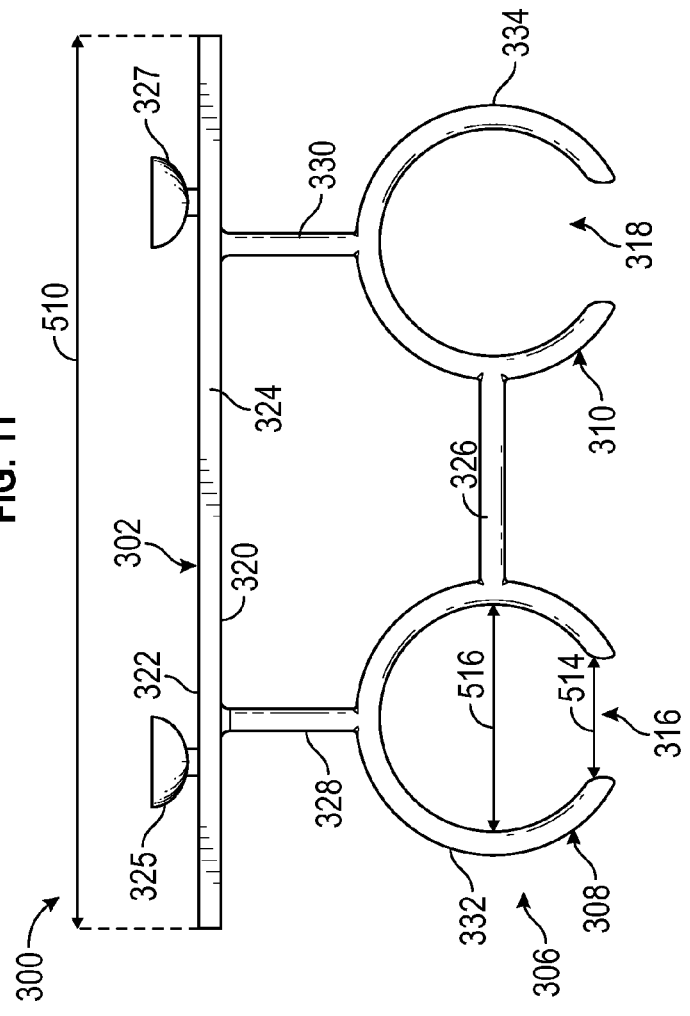

METHOD AND APPARATUS FOR A PROSTHETIC STAND

FIELD

The present disclosure generally relates to prosthetic stands for lower-extremity prosthetics, and in particular to prosthetic stands for storing lower-extremity prosthetics that are mobile, accessible and attachable.

BACKGROUND

A prosthetic is a functional replacement for an amputated or congenitally malformed or missing limb of an individual. In particular, lower-extremity prosthetics are artificially replaced limbs located at the hip level or lower of the individual. A recent study conducted about ten years ago found a world-wide estimate of all-cause lower-extremity amputations of 2.0-5.9 per 10,000 individuals. As such, there a large number of individuals that wear lower-extremity prosthetics.

Typically, individuals who wear lower-extremity prosthetics must remove their prosthetics when bathing or sleeping which requires that their prosthetic(s) be stored or placed in a location that is close and easily reachable to the individual. Although prosthetics may be stored on the bed with the individual, such an arrangement may be undesirable if the prosthetics crowd the individual and/or their sleeping partner, while placing the prosthetics on the floor alongside the bed may make prosthetics difficult to reach when the individual wants to reattach the prosthetics. Similarly, storing and reattaching prosthetics when bathing presents similar issues to individuals with lower extremity prosthetics who must store and retrieve their prosthetics using stands or other storage means that are neither easily accessible nor sufficiently mobile.

As such, there is a need for improvements in prosthetics stands that permit for easy storage, use, and access of lower extremity prosthetics by the individual.

BRIEF DESCRIPTION OF THE DRAWINGS

FIG. 9 is a perspective view of another embodiment of the prosthetic stand;

FIG. 10 is a front view of the mobile prosthetic stand of FIG. 9;

FIG. 11 is a rear view of the mobile prosthetic stand of FIG. 9;

FIG. 12 is a top view of the mobile prosthetic stand of FIG. 9;

Corresponding reference characters indicate corresponding elements among the view of the drawings. The headings used in the figures do not limit the scope of the claims.

DETAILED DESCRIPTION

Figure 1:
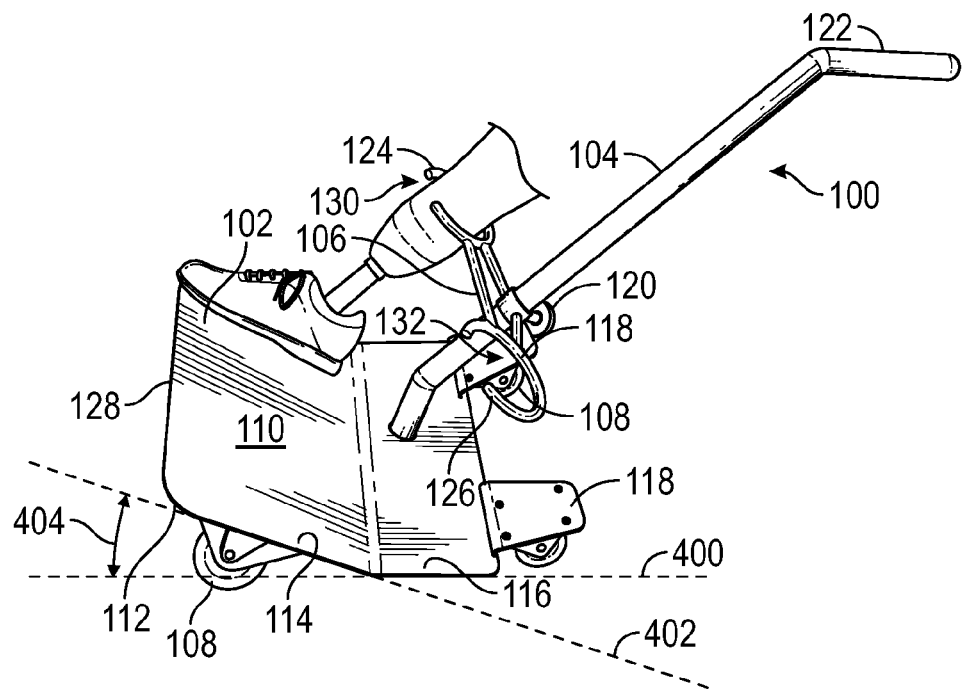
FIG. 1 is a perspective view of an embodiment of a prosthetic stand.
Figure 2:
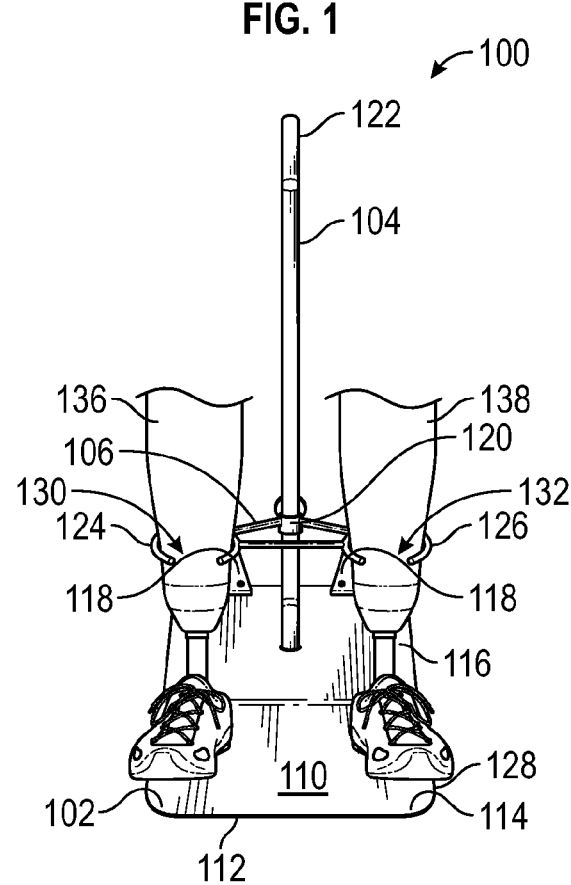
FIG. 2 is a front view of the mobile prosthetic stand of FIG. 1.

Various embodiments for a prosthetics stand that are mobile and transportable, easily accessible to the individual for storage of lower-extremity prosthetics, and/or attachable to different types of structural elements are disclosed. In some embodiments, the prosthetics stand may include a substantially flat base with an upward post extending from the base that is coupled to a holder component for storage of lower extremity prosthetics. In some embodiments, the underside of the base may include wheels that allow the prosthetics stand to be mobile. In some embodiments, the holder component is configured to secure a pair of lower-extremity prosthetics through respective first and second holders that each form an open-ring configuration configured to allow each prosthetic to be easily coupled to the holder component for storage. In some embodiments, a portion of the base may be angled relative to another portion of the base to permit the individual to easily reattach the stored prosthetics in a more natural and convenient manner. In some embodiments, the prosthetics stand includes a securing mechanism that allows the prosthetic stand to be attached to a structural surface, such as a bed or bathtub, for fixing the prosthetics stand in position, thereby permitting easier access and storage of lower-extremity prosthetics during certain activities by the individual. As used herein, the term "proximal" means that portion of the prosthetics stand closest to the individual, while the term "distal" means that portion of the prosthetics stand farthest from the individual. Referring to the drawings, embodiments of a prosthetics stand are illustrated and generally indicated as 100, 200, 300 and 400 in FIGS. 1-17, respectively.

Referring to FIGS. 1-4, one embodiment of the prosthetics stand, designated 100, includes a base 102 having a post 104 that extends upwardly from the base 102 to provide a means for handling the prosthetics stand 100 by an individual. In some embodiments, the underside of the base 102 may include four wheels 108, such as caster wheels, that permit the prosthetics stand to be easily moved along a substantially flat surface by the individual. In some embodiments, a locking mechanism (not shown) may be used to lock the caster wheels 108 in place to prevent movement and fix the prosthetics stand 100 in position. In some embodiments, a pair of wheel covers 118 may extend from the base 102 to provide a protective cover to the rear wheels 108. As shown, the post 104 defines a distal portion engaged or formed integral with the base 102 and a proximal portion that forms a handle 122 to provide a gripping surface for the individual to grip and handle the prosthetics stand 100.

In some embodiments, a holder component 106 is securely coupled along the length of the post 104 and is configured to secure and store a pair of prosthetic legs 134 and 136, respectively. The holder component 106 includes a first holder 124 and a second holder 126 that collectively extend from the post 104 with the first holder 124 and second holder 126 each configured to secure a respective prosthetic leg 134 and 136.

Figure 4:
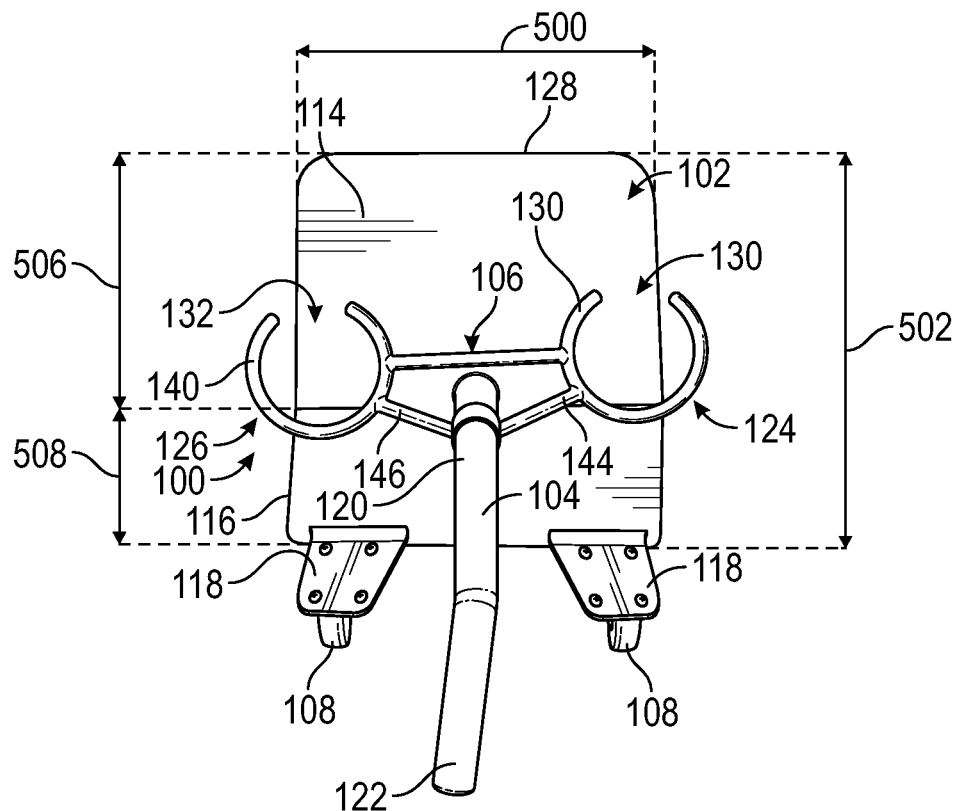
FIG. 4 is a top view of the mobile prosthetic stand of FIG. 1.
Figure 5:
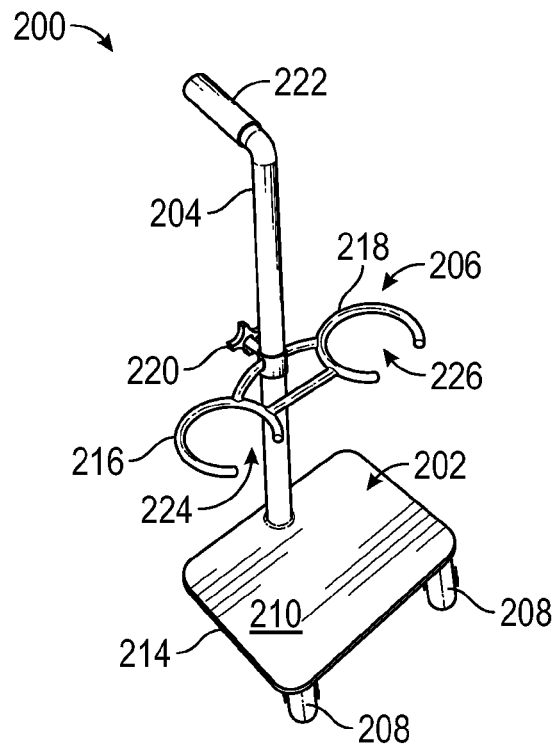
FIG. 5 is a perspective view of another embodiment of the prosthetic stand.
Figure 6:
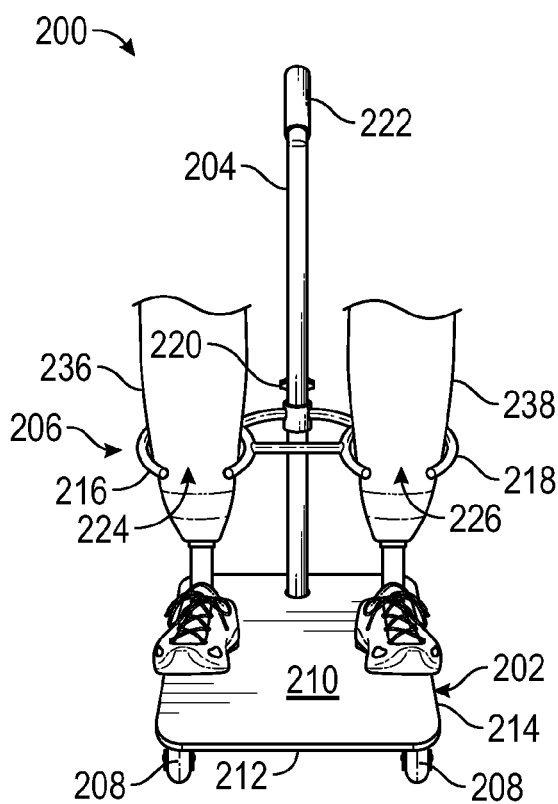
FIG. 6 is a front view of the mobile prosthetic stand of FIG. 5.

Referring to FIG. 4, in some embodiments the first holder 124 of the holder component 106 defines a first circular portion 138 having a first extension bar 144 that extends outwardly from the post 104 and the second holder 126 similarly defines a second circular portion 140 having a second extension bar 146 that also extends outwardly from the post 104. In some embodiments, the first circular portion 138 forms an opening slot 130 configured to allow the first prosthetic leg 134 to pass through the opening slot 130 and be retained within the confines of the first holder 124. Similarly, the second circular portion 140 forms an opening slot 132 configured to allow the second prosthetic leg 136 to pass through the opening 132 and be retained within the confines of the second holder 126. In some embodiments, the holder component 106 may include a connecting bar 142 that provides a structural connection and reinforcement between the first and second holders 124 and 126. As shown in FIG. 4, the circular portion of the at least one holder partially extends horizontally across the base such that the circular portion partially overlaps the fold and the angled portion of the base.

Figure 3:
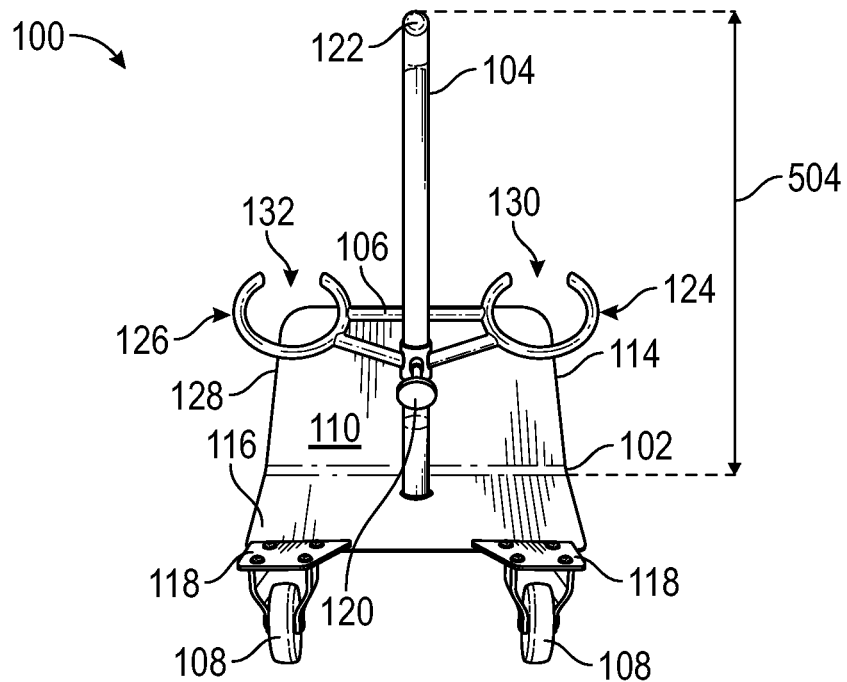
FIG. 3 is a rear view of the mobile prosthetic stand of FIG. 1.

As shown in FIG. 3, the holder component 106 further includes a clamping mechanism 120 that permits the holder component 106 to be secured at different positions along the post 104, thereby accommodating different sizes of prosthetic legs having varying lengths that can be coupled to the prosthetics stand 100. In some embodiments, the clamping mechanism 120 may be a knob that is operatively connected to a clamp, or friction/lever clamp, engaged to the post 104 in which rotation of the knob, or release of the friction/lever clamp, by the individual permits the clamp to be either loosened or tightened relative to the post 104 in order to adjust the height of the holder component 106 relative to the base 102.

In some embodiments, the base 102 may define an upper surface 110 and an opposite lower surface 112 that collectively form a peripheral edge 128 having either a rectangular or square-shaped configuration. In addition, the base 102 defines a flat portion 116 that connects to the post 104 and an angled portion 114 that extends from the flat portion 116 and forms the part of the base 102 farthest from the post 104. As shown in FIG. 1, the flat portion 102 may be oriented along an axis 400 that is substantially parallel to the surface in which the prosthetics stand 100 is standing, while the angled portion 128 may be angled at an axis 402 that forms an angle 404 relative to axis 400. As shown, the angled portion 128 provides an angled surface configured to receive and orient the foot portion of each prosthetic leg 134 and 136 such that each prosthetic leg 134 and 136 may be better angled to provide for easier attachment or detachment by the individual. In some embodiments, the angled portion 128 may form an angle 404 in the range between 1 to 90 degrees relative to the flat portion 116 of the base 102.

Referring to FIGS. 5-8, another embodiment of the prosthetics stand, designated 200, includes a base 202 having a post 204 that extends upwardly from the base 202 to provide a means for handling the prosthetics stand 200 in a manner similar to the prosthetics stand 100. In some embodiments, the underside of the base 202 includes four wheels 208 that permit the mobile prosthetics stand 200 to be easily moved along a substantially flat surface by the individual. As shown, the post 204 defines a distal portion engaged or formed integral with the base 202 and a proximal portion that forms a handle 222 to provide a gripping surface for the individual to grip and handle the prosthetics stand 200.

Similar to the holder component 106 of the prosthetics stand 100, holder component 206 is securely coupled along the length of the post 204 and is configured to secure and store a pair of prosthetic legs 130 and 132, respectively. The holder component 206 includes a first holder 216 and a second holder 218 that extend from the post 204 with the first holder 216 and second holder 218 each configured to secure a respective prosthetic leg 234 and 236.

Figure 8:
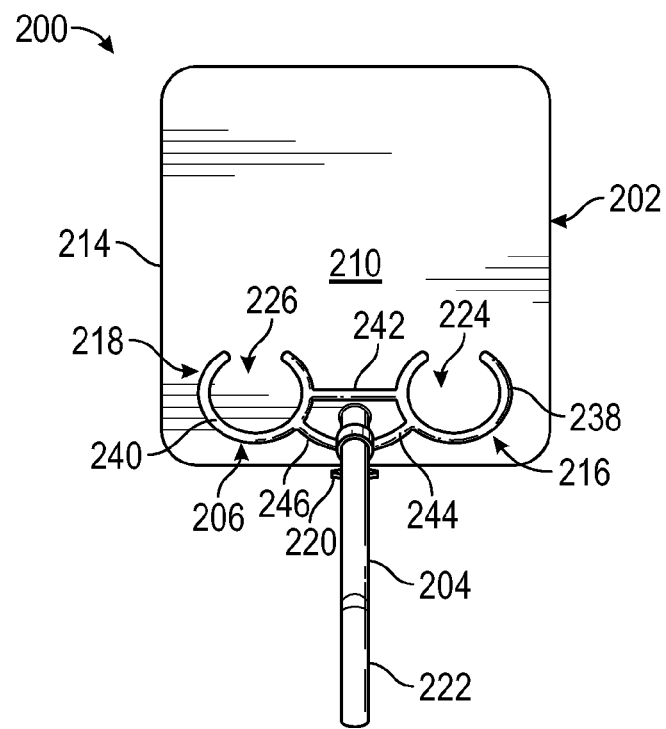
FIG. 8 is a top view of the mobile prosthetic stand of FIG. 5.
Figure 13:
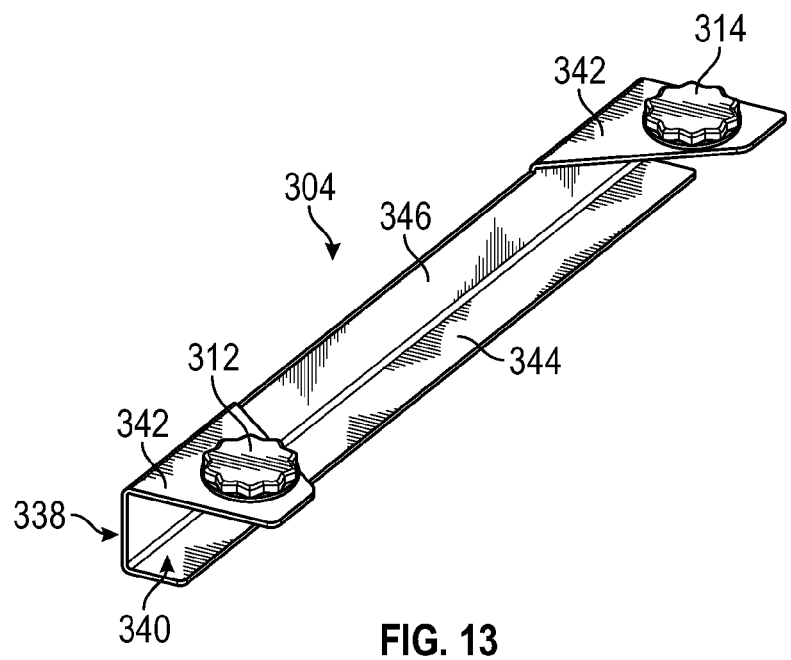
FIG. 13 is a perspective view of a retainer plate of the mobile prosthetic stand shown in FIGS. 9-12.
Figure 14:
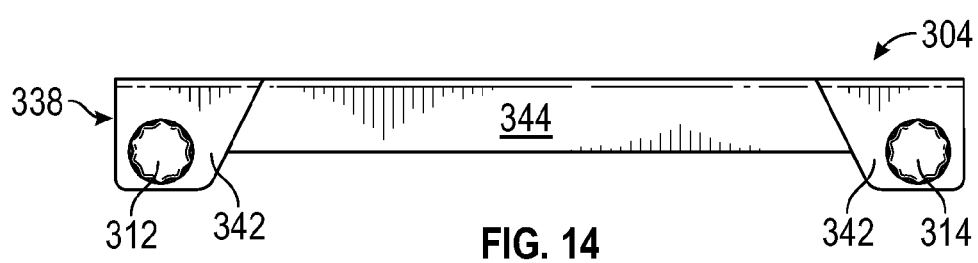
FIG. 14 is a front view of the retainer plate shown in FIG. 13.
Figure 15:
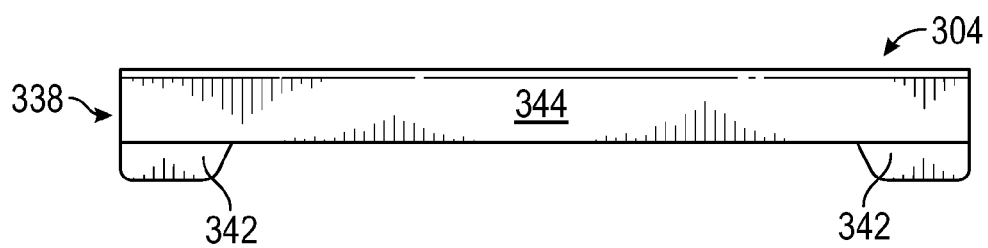
FIG. 15 is a rear view of the retainer plate shown in FIG. 13.

Referring to FIG. 8, the first holder 216 of the holder component 206 defines a first circular portion 238 having a first extension bar 244 that extends outwardly from the post 204, while the second holder 218 defines a second circular portion 240 having a second extension bar 246 that also extends outwardly from the post 204. The first circular portion 238 forms an opening slot 224 configured to allow the first prosthetic leg 236 to pass through the opening slot 224 and be retained within the confines of the first holder 216. Similarly, the second circular portion 240 forms an opening slot 226 configured to allow the second prosthetic leg 238 to pass through the opening slot 226 and be retained within the confines of the second holder 218. In some embodiments, the holder component 206 may include a connecting bar 242 that provides a structural connection and reinforcement between the first holder 216 to the second holder 218.

Figure 7:
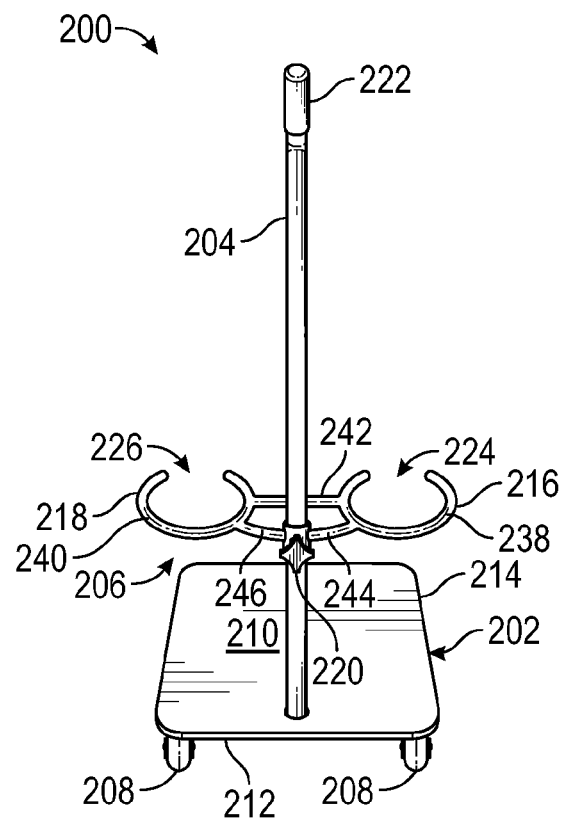
FIG. 7 is a rear view of the mobile prosthetic stand of FIG. 5.

As shown in FIG. 7, the holder component 206 further includes a clamping mechanism 220 that permits the holder component 206 to be secured at different positions along the post 204, thereby accommodating different sizes of prosthetic legs having varying lengths that can be coupled to the prosthetics stand 200. In some embodiments, the clamping mechanism 220, similar to clamping mechanism 120, may include a knob that is operatively connected to a clamp engaged to the post 204 in which rotation of the knob permits the clamp to be either loosened or tightened relative e to the post 204 in order to adjust the height of the holder component 206 relative to the base 202.

In some embodiments, the base 202 may define an upper flat surface 210 and an opposite lower flat surface 212 that collectively form a peripheral edge 228 having either a square or rectangular-like configuration. Unlike base 102 that defines a flat portion and an angled portion, the base 202 of prosthetics stand 200 defines only a flat portion 230 that connects to the bottom portion of post 204.

Referring to FIGS. 9-16, another embodiment of a prosthetics stand, designated 300, is configured to be directly attached to a structural element, such as a bed, during use. In one embodiment, the prosthetics stand 300 includes a rectangular-shaped holder plate 302 that is configured to be secured to a bed skirt 301 (FIG. 9), or the like, through a retainer plate 304 (FIGS. 9, 10, 13-16) that wedges or otherwise secures the holder plate 302 to the bed skirt 301 as shall be discussed in greater detail below. In some embodiments, the holder plate 302 defines a rear surface 322 and a front surface 320 that collectively define a peripheral edge 324. In other embodiments, the holder plate 302 may be square-shaped, oval-shaped, or circular-shaped. The front surface 320 of the holder plate 302 includes a holder component 306 that extends outwardly from the front surface 320 of the holder plate 302 and is configured to be coupled to one or more prosthetic legs 336. As shown in FIGS. 11 and 12, in other embodiments the holder plate 302 may be alternatively secured to the bed skirt 301 (FIG. 9) without using the retainer plate 304 using a pair of suction cups 325 and 327 secured to the rear surface 322 of the holder plate 302 that may be attached directly to the bed skirt 301.

Similar to holder components 106 and 206, holder component 306 of prosthetics stand 300 includes at least a first holder 308, and in some embodiments, the prosthetics stand 300 may also include a second holder 310 each configured to secure a respective prosthetic leg 336 therein. The first holder 308 includes a first circular portion 332 that extends outwardly from the base 302 through a first extension bar 328. Similarly, the second holder 310 includes a second circular portion 334 that also extends outwardly from the base 302 through a second extension bar 330. In some embodiments, the first circular portion 332 forms an opening slot 316 configured to allow the prosthetic leg 336 to pass through the opening slot 316 and be retained within the confines of the first holder 308. Similarly, in some embodiments, the second circular portion 334 forms an opening slot 318 configured to allow another prosthetic leg 336 to pass through the opening slot 318 and be retained within the confines of the second holder 310. In some embodiments, the holder component 306 may include a connecting bar 326 that provides structural connection and reinforcement between the first holder 308 and the second holder 310.

Figure 16:
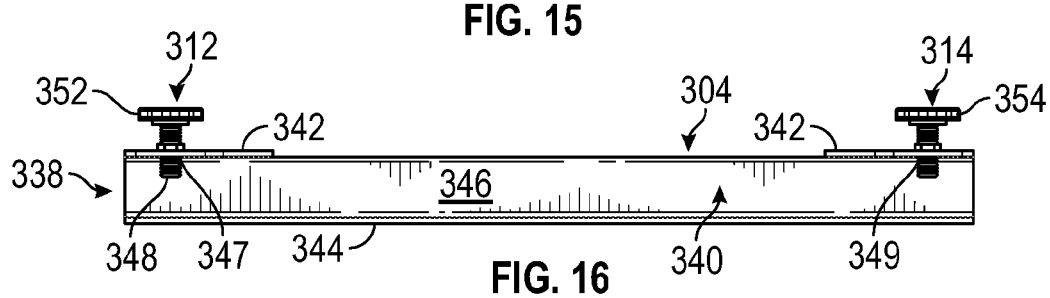
FIG. 16 is a bottom view of the retainer plate shown in FIG. 13.

As noted above, the prosthetics stand 300 includes a retainer plate 304 that is operable to secure the holder plate 302 to a bed skirt 301. As shown in FIGS. 13-16, the retainer plate 304 includes an elongated body 338 having a front portion 342, rear portion 344 and top portion 346 that collectively define a slot 340 configured to receive a portion of the bed skirt 301 and holder plate 302 therein. Referring to FIG. 16, the front portion 342 of the retainer plate 304 defines a first opening 347 and a second opening 349 configured to receive a first securing mechanism 312 and a second securing mechanism 314, respectively, which are operable to collectively apply pressure to the holder plate 302 and bed skirt 301 such that the holder plate 302 becomes wedged between the retainer plate 304 and bed skirt 301. As further shown, the first securing mechanism 312 includes a first threaded rod 348 that extends through the first opening 347 and is operatively connected to a first rotating knob 352. The first rotating knob 352 is operable to rotate the first threaded rod 348 such that rotational movement in a first direction extends the first rotating rod into the slot 340, while rotational movement of the first rotating knob 352 in an opposite second direction retracts the first rotation rod from the slot 340. Similarly, the second securing mechanism 314 includes a second threaded rod 350 that extends through the second opening 349 and is operatively connected to a second rotating knob 354. The second rotating knob 354 is operable to rotate the second threaded rod 350 such that rotational movement in a first direction extends the second rotating rod 349 into the slot 340, while rotational movement of the second rotating knob 354 in an opposite second direction retracts the second rotation rod from the slot 340.

In some embodiments, to wedge or otherwise secure the holder plate 302 to the bed skirt 301, an individual may contact the rear surface 322 of the holder plate 302 to the bed skirt 301 proximate or adjacent to the top edge of the bed skirt 301 and then position the retainer plate 304 such that the holder plate 302 and bed skirt 301 are collectively received within the slot 340 of the retainer plate 304 as shown in FIG. 9. Once the holder plate 302 and retainer plate 304 are so positioned relative to the bed skirt 301, actuation of the first and second securing mechanisms 312 and 314 by rotating the first and second rotating knobs 352 and 354 causes the first and second threaded rods 348 and 350 to engage and wedge the holder plate 302 between the bed skirt 301 and retainer plate 304, thereby securing the prosthetics stand 300 to the bed skirt 301 and making it ready for use to hold one or more prosthetics 336.

Figure 17:
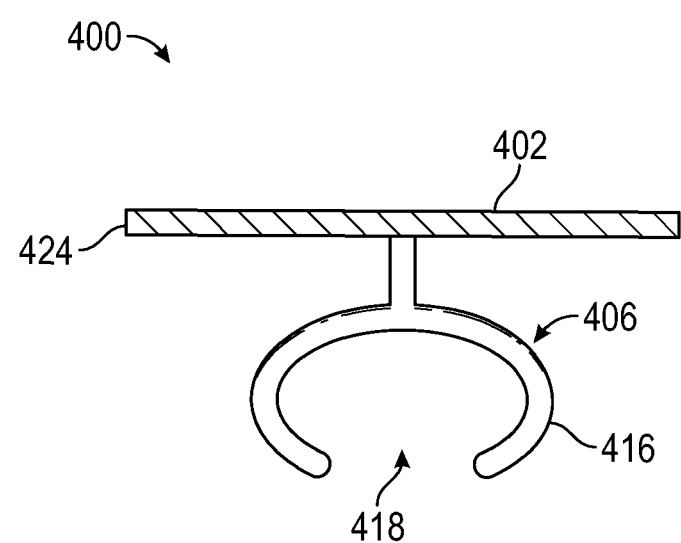
FIG. 17 is a top view of another embodiment of the prosthetic stand having a single holder.

Referring to FIG. 17, another embodiment of the prosthetics stand, designated 400, is configured to store a single prosthetic leg (not shown). As shown, the prosthetics stand 400 includes a holder plate 402 having holder component 406 with only a single holder 416. Similar to the holders described above, the single holder 416 defines an opening 418 configured to permit passage of a prosthetic leg (not shown) therethrough such that the prosthetic leg is retained within the single holder 416. Similar to prosthetics stand 300, prosthetics stand 400 is secured to a bed skirt 301 using the retainer plate 304 described above.

In some embodiments, the prosthetics stand 100 may be manufactured using the following dimensions a length 500 of 15 inches, a width 502 of 16 inches and a height 504 of 27 inches. In some embodiments, the angled portion 114 of base 102 may have a length 506 of 11 inches and the flat portion 116 of holder plate 102 may have a length 508 of 6 inches. In some embodiments, the prosthetic stand 200 may have similar dimensions as prosthetics stand 100. In some embodiments, the holder plate 302 of prosthetic stand 300 may have a length 510 of 20 inches and a height 512 of 3 inches. In some embodiments, the first and second holders, 124, 126, 216, 218, 308, and 310 may have an inner dimension 516 of 6 inches and the slot openings 130, 132, 224, 226, 316, and 318 may have a length 514 of 3 inches, although other embodiments may have different dimensions to accommodate prosthetic legs having different sizes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A prosthetics stand comprising:
   a base having an upper surface and a lower surface, the base comprising a fold that extends across a length of the base between a flat portion and an angled portion of the base, wherein the flat portion extends along a first axis and the angled portion extends along a second axis;
   a post defining a proximal portion and a distal portion, wherein the distal portion of the post is engaged to the upper surface of the flat portion of the base; and
   a holder component coupled to the post, the holder component comprising at least one holder forming a circular portion that defines an opening slot, the opening slot comprising permanent space between opposing endpoints of the circular portion,
   wherein the angled portion of the base extends upwardly from the flat portion of the base with an obtuse angle defined over the upper surface of the base at an intersection between the angled portion of the base and the flat portion of the base, and
   wherein the circular portion of the at least one holder partially extends horizontally across the base such that the circular portion partially overlaps the fold and the angled portion of the base.

2. The prosthetics stand of claim 1, wherein the holder component is operable to be coupled along different lengths of the post relative to the base.

3. The prosthetics stand of claim 2, wherein the proximal portion of the post defines a handle.

4. The prosthetics stand of claim 1, further comprising:
a clamping mechanism operable to secure the holder component to predetermined positions along different lengths of the post.

5. The prosthetics stand of claim 4, wherein the clamping mechanism comprises a knob and clamp arrangement, wherein rotation of the knob in a direction tightens the clamp mechanism and rotation of the knob of the clamp mechanism in an opposite direction loosens the clamp mechanism.

6. The prosthetics stand of claim 1, wherein each opening slot is configured to allow a lower-extremity prosthetic to pass through and be retained within the respective at least one holder.

7. The prosthetics stand of claim 1, wherein the upper surface and lower surface of the base collectively define the flat portion extending along the first axis and the angled portion is in communication with the flat portion and extending along the second axis, the second axis being different from the first axis.

8. The prosthetic stand of claim 1, further comprising:
a plurality of wheels attached along an underside of the base to permit the prosthetics stand to move along a surface.

9. A method of manufacturing a prosthetics stand comprising:
forming a base having an upper surface and a lower surface, the base comprising a flat portion and an angled portion extending upwardly from the flat portion;
coupling a post to the upper surface of the base, wherein the post defines a proximal portion and a distal portion;
forming a holder component having one or more holders, each of the one or more holders defining a respective opening slot configured to allow a prosthetic to pass through the respective opening slot and be retained within confines of the respective one or more holders, the respective opening slot of the each of the one or more holders comprising permanent space between opposing endpoints of the each of the one or more holders; and
coupling the holder component at a position along the post,
wherein the holder component partially overlaps the angled portion of the base.

10. The method of claim 9, further comprising:
forming the base having the flat portion oriented along a first axis and the angled portion oriented along a second axis, wherein an angle is formed between the first axis and the second axis.

11. The method of claim 10, wherein an obtuse angle is formed between the angled portion of the base and the flat portion of the base over the upper surface of the base.

12. The method of claim 9, further comprising:
attaching a plurality of wheels to an underside of the base.

13. A prosthetics stand comprising:
a base defining a flat portion and an angled portion extending upwardly from the flat portion; and
a holder component coupled to the base, the holder component including a first holder and a second holder each defining a circular portion that forms an opening slot configured to allow a lower-extremity prosthetic to pass through and be retained within confines of the respective first and second holders, the opening slot comprising permanent space between opposing endpoints of the circular portion,
wherein the holder component extends partially over the angled portion of the base.

14. The prosthetics stand of claim 13, further comprising a fold between the flat portion and the angled portion of the base.

* * * * *